United States Patent [19]

Granite

[11] 4,196,728
[45] Apr. 8, 1980

[54] BREATHING APPARATUS

[76] Inventor: Alfred D. Granite, 2320 41st St., NW., Washington, D.C. 20007

[21] Appl. No.: 938,756

[22] Filed: Sep. 1, 1978

[51] Int. Cl.[2] .................... A61M 15/00; A62B 7/00
[52] U.S. Cl. ........................... 128/201.13; 128/204.17
[58] Field of Search ............... 128/212, 145 R, 142.6, 128/139; 165/DIG. 18; 62/285

[56] References Cited

U.S. PATENT DOCUMENTS

| 1,603,021 | 4/1898 | Dight | 177/171 |
| 2,876,631 | 3/1959 | Bailey | 62/285 |
| 3,295,522 | 1/1967 | Johnson | 128/212 |
| 3,326,214 | 6/1967 | McCoy | 128/212 |
| 3,333,585 | 8/1967 | Barghini et al. | 128/212 |
| 3,609,941 | 10/1971 | Eldredge | 54/80 |
| 3,707,966 | 2/1973 | Nebel | 128/212 |
| 3,747,598 | 7/1973 | Cowans | 128/142 |
| 4,044,531 | 8/1977 | Marchello et al. | 54/80 |

FOREIGN PATENT DOCUMENTS 2436436  3/1965  Fed. Rep. of Germany .......... 128/212

*Primary Examiner*—Robert W. Michell
*Assistant Examiner*—Thomas Wallen

[57] ABSTRACT

A breath warming apparatus which comprises a flexible, lightweight casing in the shape of a curved, generally symmetrical horn of expanding cross section, having a flared internal chamber containing metal mesh. This mesh will retain the heat and expired moisture of the wearer and will in turn warm and humidify the air being inhaled through the device. A mouthpiece, designed to minimize resistance to airflow to and from the oral cavity, provides the immediate aperture through which the user breathes when using the apparatus. Relatively large exit ports allow for high volume transfer of air.

7 Claims, 4 Drawing Figures

BREATHING APPARATUS

BACKGROUND OF THE INVENTION

This invention relates generally to a breath warming apparatus, and more particularly relates to a lightweight breathing apparatus particularly suited for use in cold weather and under conditions where the apparatus must warm relatively large quantities of air at high respiration rates.

It is well known that inhalation of cold, dry air can be uncomfortable and can impair the functioning of the upper respiratory tract. Particular difficulties may be encountered under extreme conditions of cold weather by the human respiratory tract in the removal of foreign matter and in the movement of mucus away from the lungs to be ultimately expelled from the respiratory tract. Where high flow rates of cold air are encountered, furthermore, such as experienced during the deep, rapid respiration which generally accompanies prolonged strenuous physical exercise under ambient temperatures of, say, 0° C. or below, this functioning of the respiratory tract may be even further impaired.

The concept of using the exhaled breath to supply heat and humidity to aid in the natural conditioning process has been known for some time. However, prior devices have generally been unsuitable for using during strenuous physical exercise or by athletes because of one or more shortcomings. For example, the devices are generally too heavy, or too confining and uncomfortable, or they permit high respiration rates only at the expense of excessive breathing effort. Lack of simplicity of manufacture and of use have also plagued prior designs.

In order to overcome these and other deficiencies in the known prior art devices, a breath warming apparatus has been developed which is suitable for use by athletes or others and which can be inexpensively and simply manufactured. The apparatus is effective in humidifying and warming inhaled air at high respiration rates and under conditions wherein the ambient temperature is, for instance, substantially below 0.C., even under high wind conditions. It is rugged, requiring little maintenance or special care, and it is designed to protect the teeth, jaw, and lower face of the wearer from injury in the event of a fall or if a sharp blow is directed to the lower face. Excessive heat loss from the oral cavity and lower face is prevented or minimized and protection to the lower face from the effects of crosswinds is provided. Because of its unique design wherein the air intake mechanism is disposed on the side of the face in a direction away from forward motion by the wearer, freezing of condensed moisture, which might otherwise impair the capacity of the device when used by, for instance, a jogger, is minimized. Also, forced induction of cold air, where the jogger is running into the wind, is minimized. The air intake mechanism is, furthermore, so disposed that condensation of moisture expelled from the lungs of the user occurs away from the front of the face, preventing the "fogging up" of the eyeglasses that are frequently worn by joggers.

Even when it is used at high respiration rates, the instant apparatus will not materially increase breathing effort. It is furthermore designed to automatically dispose of excess breath condensate without the risk of freezing and attendant clogging of air passageways, and, while warming and humidifying inhaled air, it will also filter and collect airbound particulate matter and prevent it from being exhaled.

SUMMARY OF THE INVENTION

As shown in the accompanying drawings, the respirator essentially comprises a flexible, lightweight casing in the shape of a curved, generally symmetrical horn of expanding cross section, having a flared internal chamber containing metal mesh. This mesh will retain the heat and expired moisture of the wearer and will, in turn, warm and humidify the air being inhaled through the device. A mouthpiece, designed to minimize resistance to airflow to and from the oral cavity, provides the immediate aperture through which the user breathes when using the apparatus. Relatively large exit ports allow for high volume transfer of air. In use, the apparatus may be secured in place by the use of elastic straps extending around the head and neck.

BRIEF DESCRIPTION OF THE DRAWINGS

Details of the invention and an appreciation of its utility will be facilitated by referring to the accompanying drawings, in which.

DESCRIPTION OF THE PREFERRED EMBODIMENT

Figure 1:
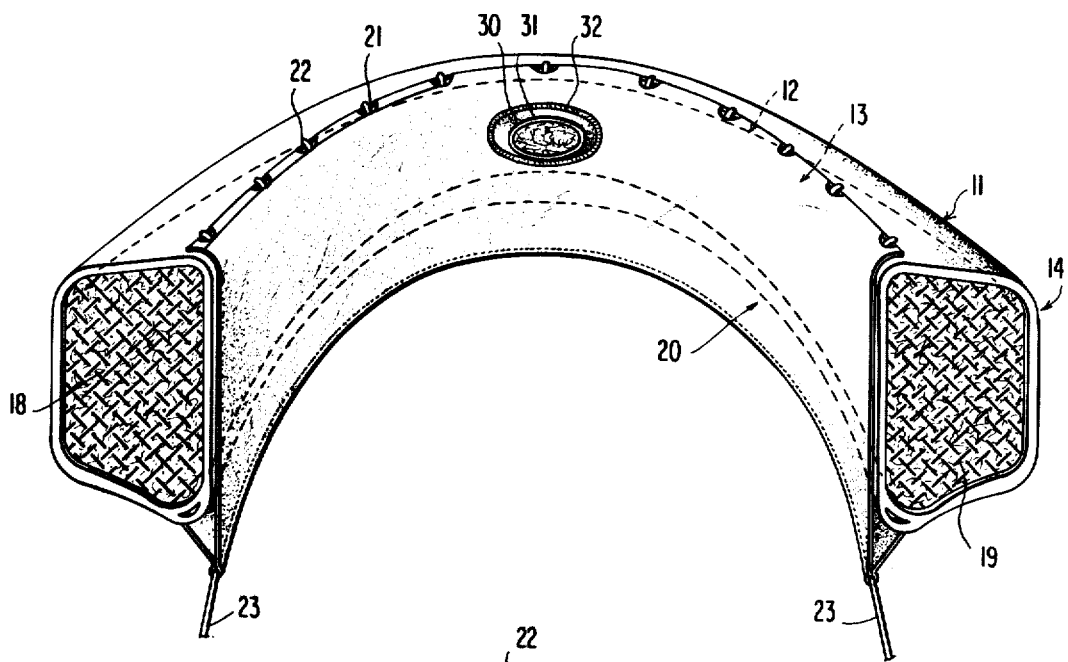
FIG. 1 is a perspective view of the respirator, without the support harness, as seen from the rear.
Figure 2:
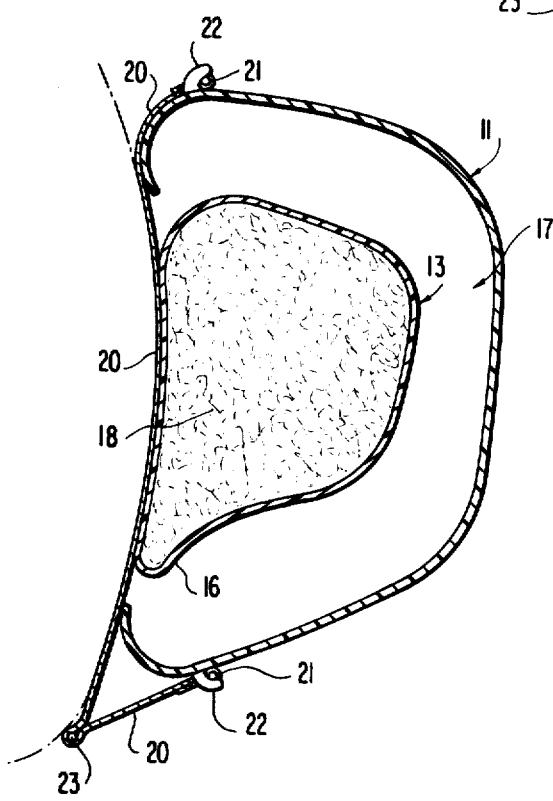
FIG. 2 is a vertical cross-sectional view of the respirator at a point approximately midway between the mouthpiece and the exit port.
Figure 3:
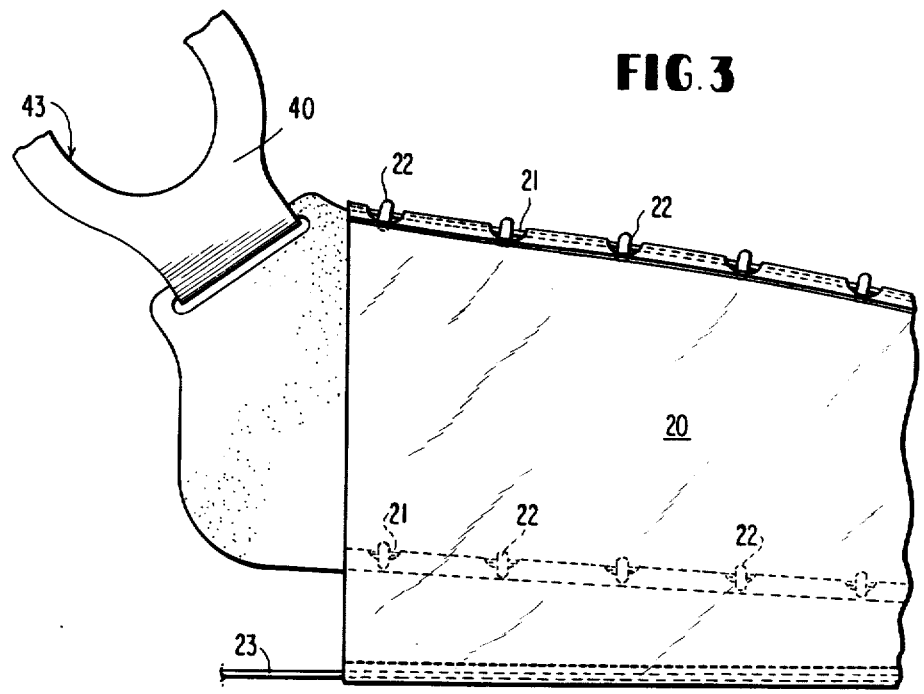
FIG. 3 is a side view of the respirator, showing that portion of the respirator which would be next to the face of the wearer.
Figure 4:
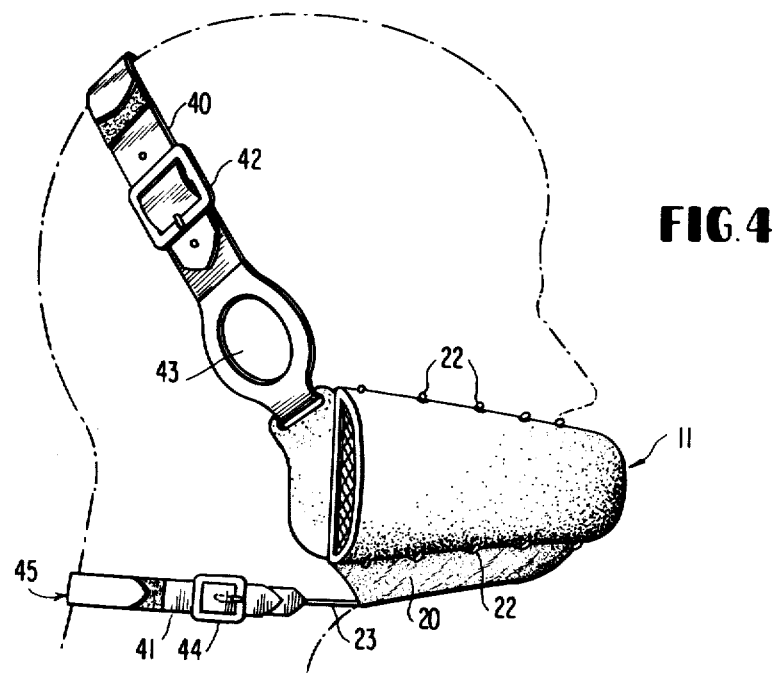
FIG. 4 is a side view of the respirator as it would appear in use, showing the wearing position and support harness.

The outer portion of the respirator is made up of a shell or casing having a generally "D" shaped cross section with the flat portion of the casing placed against the face of the wearer, as shown in FIGS. 1 and 2. Referring to FIG. 1, the side of this outer casing 11 not in direct contact with the face may be made of plastic, rubber or other lightweight material which would provide a curved structure. The outer casing should be non-moisure absorbing, have low thermal conductivity, be chemically non-reactive, and economical to manufacture. The casing 11 is shaped so that when the respirator is being worn and the mouthpiece 30 is in place, the casing will curve around both sides of the lower face and orient the ports 14 in a position roughly 1 to 3 inches below and in front of the ears as shown in FIG. 4. That portion of the outer casing which would rest directly against the cheek of the wearer is comprised of fabric 20 stretched across the opening of the casing by the use of hooks 22 attached to the shell, as shown in FIGS. 2 and 3. A flexible wire 21 sewn into the outside edge of the fabric 30 is then used to engage these hooks 22 on both the top and bottom of the shell 11. This fabric forms a type of "liner" for the device and may be easily removed for purposes of cleaning. An elastic cord 23 sewn into the bottom portion of the fabric enables the wearer to secure the fabric under the chin. The cord can serve as an anchor for the device as well as a means to keep the fabric taut and against the skin under the neck, thereby reducing heat loss to the outside. Elastic may also be used to conform the fabric around the mouthpiece.

With respect to overall size of the device, it is thought that any dimension suggested by the representation in FIG. 4 would be satisfactory so long as adequate volume and cross-sectional area for the internal cavity is provided and the casing is not so large as to become unwieldy. An exit port having a cross-sectional area of between 2 and 6 square inches is foreseen depending upon the efficiency of the metallic mesh chosen.

Formed within this outer casing 11 is a second, inner casing 12 which forms a flared tube-like cavity 13 characterized by a continuously increasing cross-sectional area from the region around the mouthpiece to the region of the ports 14. As can be seen in FIG. 2, this internal cavity 13 is intended to rest lightly on the face of the wearer along most of its length, separated from the skin by the fabric liner 20. The purpose of this orientation is twofold. By directly covering the lower face, it will tend to minimize heat loss from the oral cavity of the wearer which in severely cold weather or high wind conditions can be extreme. It will also maximize the accumulation and retardation of body heat by the metallic mesh within the internal cavity discussed below, by allowing the oral cavity to act as an additional source of heat.

While even relative dimensions are not critical, it is anticipated that this inner cavity 13 will be within the range of 0.5 to 2.5 square inches in cross-sectional area around the mouthpiece and within the range of 2 to 6 square inches in cross-sectional area at the ports, where inner and outer casings meet. This cross-sectional area has been depicted as roughly elliptical but need not be so limited so long as a well-defined path for condensation runoff is provided, as in 16 of FIG. 2. To aid in providing for such runoff, the floor of the internal cavity is designed to present a slope, which is directed downwardly and outwardly in relation to the face, when the device is in use.

It should be noted that the exterior walls of the casing 11 and the interior walls which define the cavity 13 are not common or shared walls. A space gradually decreasing to minimum dimension at port 14 separates these surfaces, and provides an air space or outer cavity 17 which acts as an insulating medium between the heat-releasing inner cavity and the heat-retaining shell. This outer cavity 17 may simply be an airtight empty cavity, or optionally, the outer cavity may be filled with a lightweight insulating material. In addition, the air space 17 can act as a cushion in the event the wearer of the device should fall or be struck near the mouth. Wall thickness would be only that necessary to give the respirator structural rigidity with a small margin of excess. It is a design object of the respirator to minimize its weight and allow liberal deformation under stress. This deformation can be either temporary or permanent depending upon the nature of the materials. It is foreseen that malleable or plastically deformable materials could be used to allow fitting of the respirator to the individual facial contours of the wearer.

The mouthpiece 30 as shown in FIG. 1 is provided at the center of the respirator forming an air passage between the internal cavity 13 and the wearer's mouth. The mouthpiece may be advantageously shaped with walls which diverge in the direction of the mouth so that in this direction the mouthpiece forms a passageway of expanding cross section. This is important in order to maximize the volume of air which can be accommodated. The mouthpiece itself may be of a kind and, for instance, may be similar to that typically used in Self Contained Underwater Breathing Apparatus ("SCUBA") and would be placed in the mouth in front of the teeth. A flexible, pleated coupling could be used to exert slight pressure against the teeth, thereby insuring a positive air seal through the mouthpiece even during periods of high physical activity. An elastic band may be used to fit the fabric liner around the mouthpiece as it protrudes from the inner cavity.

The interior of internal cavity 13 is loosely filled with a high surface area material 18 which will be capable of retaining moisture and body heat from the exhaled breath as well as heat from contact with the skin of the wearer and will be able to release that heat and moisture at a sufficient rate to warm and humidify the cold air being inhaled by the wearer through the device. It is anticipated that the high surface area material will also act as a filter for certain types of airborne particulate matter. With regard to the exact nature of this high surface area material, certain metals such as copper, bronze, aluminum or stainless steel which have been physically treated to increase effective surface area for example by shaving or shredding, are most satisfactory for this purpose from the standpoint of thermal efficiency and cost of manufacture. Chemical treating, such as chemical etching or cleaning of the metallic meshes may also prove effective. Also, sealants may be employed to render the heat exchange material inert to the environment and these sealants may be coated on the material. Use of copper or bronze would maximize the thermal efficiency of the respirator and would be the material of choice where severe weather conditions would be encountered, as in arctic wind climates. Under less demanding conditions, stainless steel may be used effectively to condition the air, and would have the additional advantage of resisting the effects of moisture, oxidation, or other undesirable chemical reactions based on respiration byproducts. It will be appreciated that various combinations of materials may be usefully employed depending upon the conditions of use. For instance, where very severe weather conditions are to be encountered, the portion of the inner cavity in the area of the mouth can advantageously be filled with, for instance, copper mesh while the portion of the inner cavity nearer the exit ports may be filled with stainless steel which is less conductive and would minimize condensation and freezing of moisture. Blends of meshes, for instance copper mesh and stainless steel mesh, may also provide advantageous results depending upon the conditions of use. A cover or screening 19 is provided to retain the high surface area material 18 in position in the inner cavity.

In use, the respirator is worn with the aid of a support harness comprising an elastic headband 40 shown in FIGS. 3 and 4, and a neckband 41 which makes use of elastic cord 23 sewn into the bottom of the fabric liner 20 and shown in FIGS. 2, 3, and 4. Referring to FIG. 4, the headband 40 would pass over the back of the head, above the ears, and would be adjustable via adjustment buckle 42. Holes 43 could be cut in the headband to accommodate the ears. Neckband 41 would pass around the neck of the wearer, and would represent an extension of elastic cord 23. Adjustment of the neckband would be via buckle 44. Both headband and neckband would be made of a material which would be comfortable against the skin and sufficiently wide to prevent irritation or excessive pressure. Fastening means such as the hook-loop fabric fasteners marketed under the name Velcro could be used to assist in placement and adjustment of the respirator, as in 45 of FIG. 4.

I claim:

1. A lightweight streamlined breath-warming apparatus designed in particular for use under conditions where high respiration rates are encountered, which comprises:
   (a) a flexible lightweight outer casing in the shape of a curved, generally symmetrical horn of expanding cross-sectional dimension which is adapted to extend from the region of the mouth of the user when in use rearwardly around and in close proximity to the lower portion of both sides of the face, the peripheral edges of said outer casing defining two exit ports each having a cross-sectional area of from about 2 to 6 square inches for the intake and outflow of a large volume of air by the user;
   (b) an inner tubular casing within said outer casing extending from the mouthpiece within said outer casing and having a generally increasing cross-sectional dimension from the region adjacent to the mouth of the user when in place to the region adjacent to the peripheral edges of said outer casing where it is joined with said peripheral edges and together with said peripheral edges defines said exit ports, the outer surface of said inner casing and the inner surface of said outer casing defining an insulating chamber, the inner surface of said inner tubular casing defining an inner cavity within which is disposed a high surface area heat conductive material which is capable of retaining heat and moisture from exhaled air of the user and which in turn is capable of transferring at least a portion of said heat and moisture to air being inhaled by said user through said exit ports;
   (c) a mouthpiece which is adapted to fit comfortably in the human mouth and which is capable of minimizing resistance to airflow to and from the oral cavity, the interior walls of said mouthpiece defining a passageway for the transfer of air to and from the oral cavity of the user to said inner cavity and ultimately to said exit port.

2. The breath-warming device of claim 1, wherein the lower and outer portion of the inner surface of said inner tubular casing contains a channel to accommodate the transfer of accumulated condensation from said inner chamber through said exit ports and away from the region of said inner chamber adjacent said mouthpiece.

3. The breath-warming device of claim 1, wherein the interior walls of said mouthpiece diverge in the direction of the mouth defining a passageway having generally increasing cross-sectional dimension from the region immediately adjacent the intersection of said passageway and said inner chamber to the region immediately adjacent to the oral cavity of the user when in use.

4. The breath-warming device of claim 1 wherein the portion of the outer casing which rests directly against the face of the user is comprised of a fabric liner which is attached to said outer casing and which is adapted to transfer body heat from the face through said fabric and said inner tubular casing into said inner cavity to assist in the heating of air which is being inhaled through said mouthpiece.

5. The breath-warming device of claim 4 wherein said fabric is removable from said outer casing for cleaning and is attached to said outer casing by means of hooks especially adapted for attachment and removal of said fabric liner.

6. The breath-warming device of claim 1 wherein said high surface area heat conductive material is a metal mesh selected from copper, bronze, aluminum and stainless steel.

7. A lightweight, portable respiration device, for use by athletes and others under conditions wherein high respiration rates are encountered, to be used in cold weather, said respiration device comprising:
   (a) a semi-flexible shell of flared cross section and which will enable the device to conform substantially to the human lower face, wherein said shell encloses a flared tube of a shape similar to that of said shell, said tube designed to be in close proximity to the face of the wearer and containing a channel to accommodate condensation runoff, the interior of said tube defining an inner cavity, and the exterior of said tube, together with the inside surface of said shell, defining an outer cavity within said shell, each flared end of said tube coinciding with the corresponding flared end of said shell to form a single port with an area of 2 to 6 square inches for the intake and outflow of the wearer's breath;
   (b) a mouthpiece, located equidistantly from each of said ports, which acts as a passageway between the wearer's mouth and said internal cavity, said mouthpiece having interior walls which diverge in the direction of the mouth;
   (c) a high surface area material comprised of one or more of copper, bronze, aluminum, or stainless steel, which is packed into said internal cavity for the purpose of retaining exhaled body heat and moisture and in turn warming, humidifying, and filtering air as it is being inhaled by the wearer.

* * * * *